United States Patent
Fay et al.

(10) Patent No.: US 7,352,465 B2
(45) Date of Patent: Apr. 1, 2008

(54) SAMPLE CONDITIONING AND ENVIRONMENTAL CONTROL TECHNIQUES FOR GAS SENSOR

(75) Inventors: Jonathan Fay, San Mateo, CA (US);
Kevin Nason, Menlo Park, CA (US);
Bhairavi Parikh, Palo Alto, CA (US);
John Hammerman, Lincoln, CA (US);
James Stone, Saratoga, CA (US);
David Anvar, Sunnyvale, CA (US)

(73) Assignee: Aperon Biosystems Corp., Menlo Park, CA (US)

( * ) Notice: Subject to any disclaimer, the term of this patent is extended or adjusted under 35 U.S.C. 154(b) by 113 days.

(21) Appl. No.: 11/053,210

(22) Filed: Feb. 7, 2005

(65) Prior Publication Data

US 2005/0240115 A1 Oct. 27, 2005

Related U.S. Application Data

(63) Continuation-in-part of application No. 10/767,709, filed on Jan. 28, 2004, and a continuation-in-part of application No. 10/334,625, filed on Dec. 30, 2002, now abandoned.

(60) Provisional application No. 60/398,216, filed on Jul. 23, 2002.

(51) Int. Cl.
*G01N 21/00* (2006.01)

(52) U.S. Cl. ................................................ 356/437

(58) Field of Classification Search ............... 250/343, 250/345; 356/437; 600/531–532
See application file for complete search history.

(56) References Cited

U.S. PATENT DOCUMENTS

| | | | | |
|---|---|---|---|---|
| 3,514,994 A | * | 6/1970 | Shaw | 73/76 |
| 3,895,630 A | * | 7/1975 | Bachman | 600/531 |
| 4,301,114 A | * | 11/1981 | Rounbehler et al. | 422/52 |
| 4,812,648 A | * | 3/1989 | Perlman | 250/255 |
| 5,340,987 A | * | 8/1994 | Eckles et al. | 250/345 |
| 5,379,654 A | * | 1/1995 | Carvajal et al. | 73/863.84 |
| 5,542,284 A | * | 8/1996 | Layzell et al. | 73/23.2 |
| 5,789,044 A | * | 8/1998 | Ram et al. | 428/35.7 |
| 5,887,784 A | * | 3/1999 | Haas | 236/44 A |
| 5,894,836 A | * | 4/1999 | Wu et al. | 126/617 |
| 6,002,817 A | * | 12/1999 | Kopelman et al. | 385/12 |
| 6,033,368 A | * | 3/2000 | Gaston et al. | 600/532 |
| 6,114,700 A | * | 9/2000 | Blades | 250/343 |
| 6,241,948 B1 | * | 6/2001 | Watkins et al. | 422/82.05 |
| 6,305,212 B1 | * | 10/2001 | Drzewiecki | 73/23.2 |
| 6,325,978 B1 | * | 12/2001 | Labuda et al. | 422/84 |
| 6,363,772 B1 | * | 4/2002 | Berry | 73/24.02 |
| 6,468,222 B1 | * | 10/2002 | Mault et al. | 600/531 |
| 6,610,263 B2 | * | 8/2003 | Pahlman et al. | 423/239.1 |

(Continued)

*Primary Examiner*—Layla G. Lauchman
*Assistant Examiner*—Jarreas Underwood
(74) *Attorney, Agent, or Firm*—Townsend and Townsend and Crew LLP.; Henry Heines (57) ABSTRACT

The present invention is a system and method of conditioning the sample and surrounding environment of an exhaled breath sensor. It includes (i) using a particular molecular sieve for a triple purpose: (a) maintaining the sensor at a constant relative humidity during storage, (b) equilibrating the incoming breath stream to the same relative humidity as the sensor, and (c) eliminating the analyte from the environment around the sensor during storage. The present invention also includes removal of interfering components from the exhaled breath, such as carbon dioxide, as well as a thermal management technique.

21 Claims, 7 Drawing Sheets

U.S. PATENT DOCUMENTS 6,635,415 B1 * 10/2003 Bollinger et al. .............. 435/4
6,740,145 B2 * 5/2004 Boroson et al. .............. 96/108
6,911,131 B2 * 6/2005 Miyazaki et al. ...... 204/403.14
2004/0110299 A1 * 6/2004 Sivavec ....................... 436/25

* cited by examiner

Figure 15

SAMPLE CONDITIONING AND ENVIRONMENTAL CONTROL TECHNIQUES FOR GAS SENSOR

RELATED APPLICATIONS

This application is a continuation in part of U.S. Application No. 10/767,709, filed 28 Jan. 2004, and is also a continuation in part of U.S. Application No. 10/334,625, filed 30 Dec. 2002, now abandoned, which claims the benefit of U.S. Provisional Application No. 60/398,216, a filed 23 Jul. 2002.

BACKGROUND OF THE INVENTION

1. Field of the Invention

This invention relates to techniques for conditioning gaseous samples and for controlling the environment in which such samples are analyzed.

2. General Background

Analysis of a subject's exhaled breath is a promising clinical tool, with potential application in the diagnosis and management of many conditions. For instance, changes in nitric oxide (NO) concentration in exhaled breath can indicate a change in the level of inflammation in the airway of an asthmatic, indicating an increase in the likelihood of an asthma attack. Excessive carbon monoxide (CO) can indicate hemolytic jaundice, and high levels of hydrogen can indicate carbohydrate malabsorption.

To quantify the concentration of gases, various sensors have been developed. Some of these sensors detect and measure changes in bioactive substances in response to a gaseous analyte. For instance, a sensor developed by the present inventors measures the optically-quantifiable changes in a sensing element comprised of sol-gel encapsulated cytochrome-c in response to NO. This sensor and related technology are disclosed in the following U.S. patent applications, the disclosures of which are hereby incorporated herein by reference: Ser. No. 10/334,625, filed 30 Dec. 2003, Ser. No. 10/767,709, filed 28 Jan. 2004, and U.S. Provisional Application No. 60/398,216 filed Jul. 23, 2002.

It is difficult to build an exhaled breath analyzer because of the interfering effects of humidity and other constituents of the ambient atmosphere and of the exhaled breath. Also, temperature variations can compromise sensor accuracy. These difficulties are especially acute when the device is designed to measure trace gases, such as NO, since the exquisite sensitivity required for such analyzers also makes the devices much more sensitive to changes in the testing conditions. Thus, any device that seeks to quantify trace analytes in exhaled breath must somehow minimize or account for these variables.

In particular, in building their NO sensor, the applicants have learned that (i) the relative humidity around the sensing element must be controlled during storage to preserve the sensor's reactivity and sensitivity, (ii) the relative humidity of the gas stream (exhaled breath) must be controlled with the relative humidity of the sensor, (iii) the sensor should be stored in an environment substantially free of the analyte of interest, such as NO, (iv) the incoming stream of exhaled breath may need to be scrubbed or purged of interfering breath components, such as carbon dioxide, and (v) the sensor is susceptible to temperature variations, and therefore the temperature of the sensor must be set and controlled at a predetermined level.

By conditioning and controlling the exhaled breath sample and the sensor's environment, a workable, commercially-viable trace gas exhaled breath sensor can be manufactured.

SUMMARY OF THE INVENTION

The present invention is a system and method of conditioning the sample and controlling the environment of an exhaled breath sensor. It includes using a particular molecular sieve for a triple purpose: (a) maintaining the sensor at a constant relative humidity during storage, (b) equilibrating the incoming breath stream to the same relative humidity as the sensor, and (c) eliminating the analyte from the environment around the sensor during storage. The present invention also includes removal of interfering components from the exhaled breath, such as carbon dioxide. Finally, the present invention includes controlling the temperature of the sensor to ensure reliable, predictable sensor performance.

DETAILED DESCRIPTION

The present invention is a system and method of conditioning the sample and surrounding environment of an exhaled breath sensor. It is designed for use with sensors that have sensing elements that are affected by humidity, or that are affected by storage in an environment that contains the analyte of interest (such as NO), or that are affected by interfering substances in the gas sample, such as carbon dioxide, or that are susceptible to temperature variations.

Figure 1:
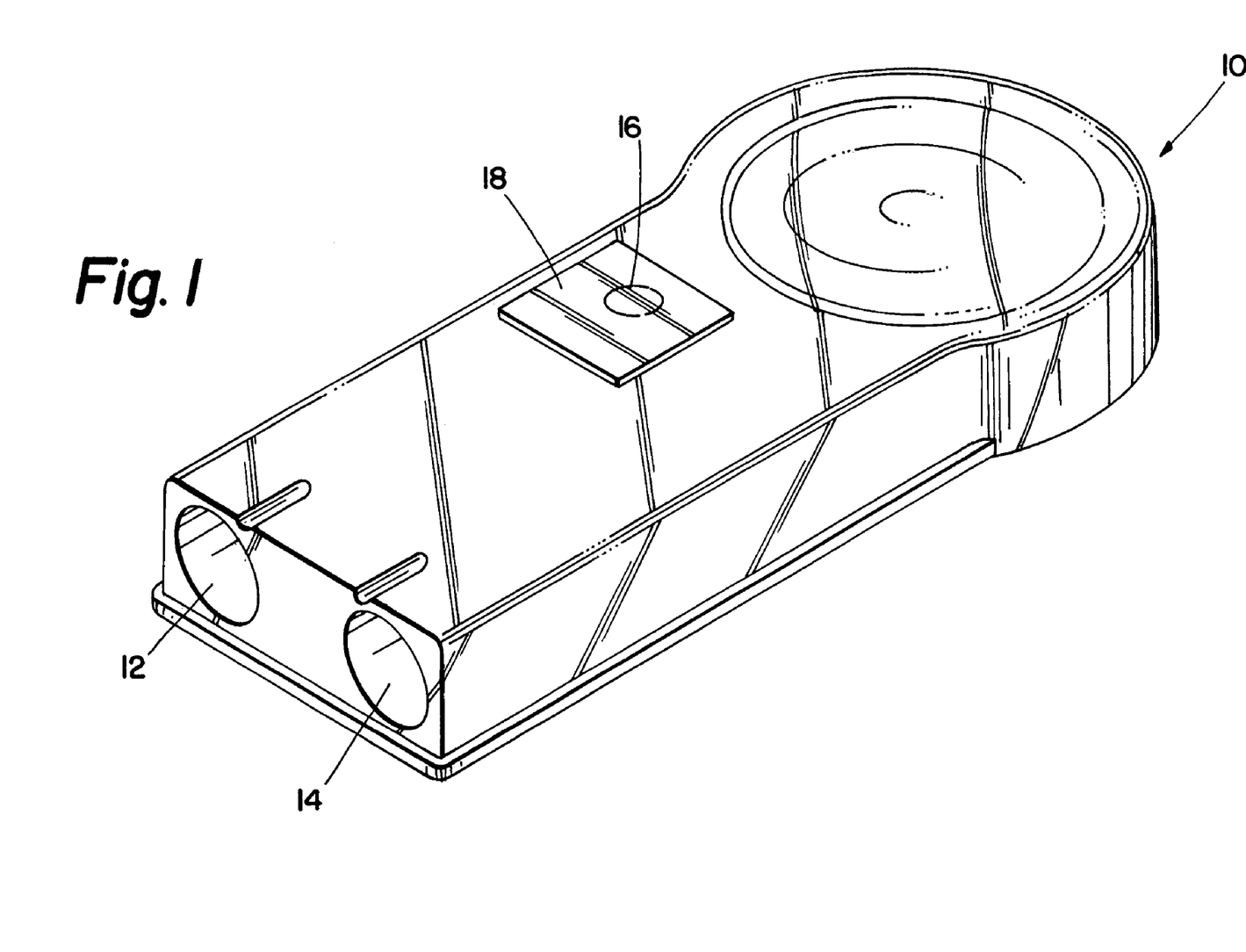
FIG. 1 is a perspective view of a sensor according to an embodiment of the present invention.
Figure 2:
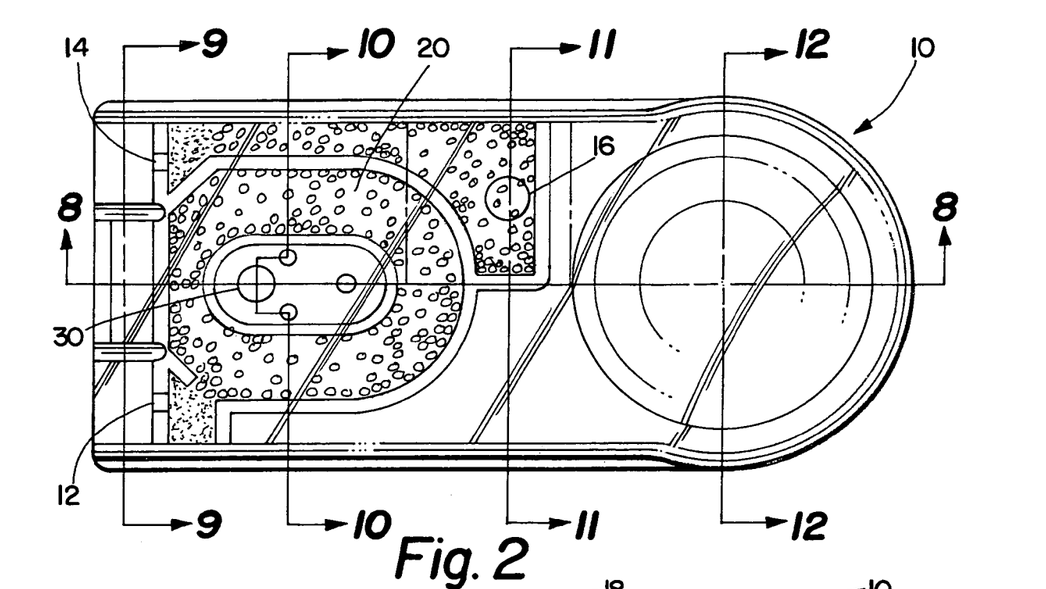
FIG. 2 is a top view of a sensor according to an embodiment of the present invention.
Figure 3:
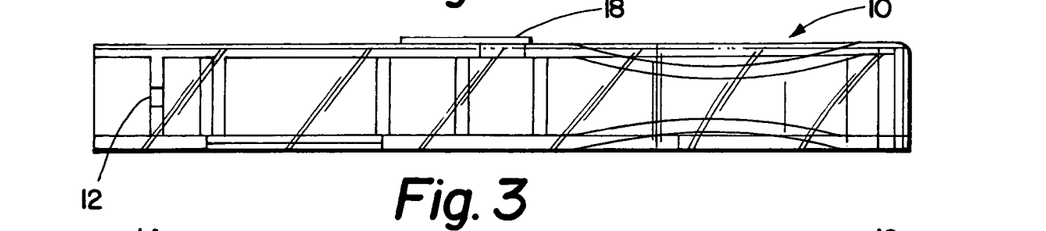
FIG. 3 is a side view of a sensor according to an embodiment of the present invention.
Figure 4:
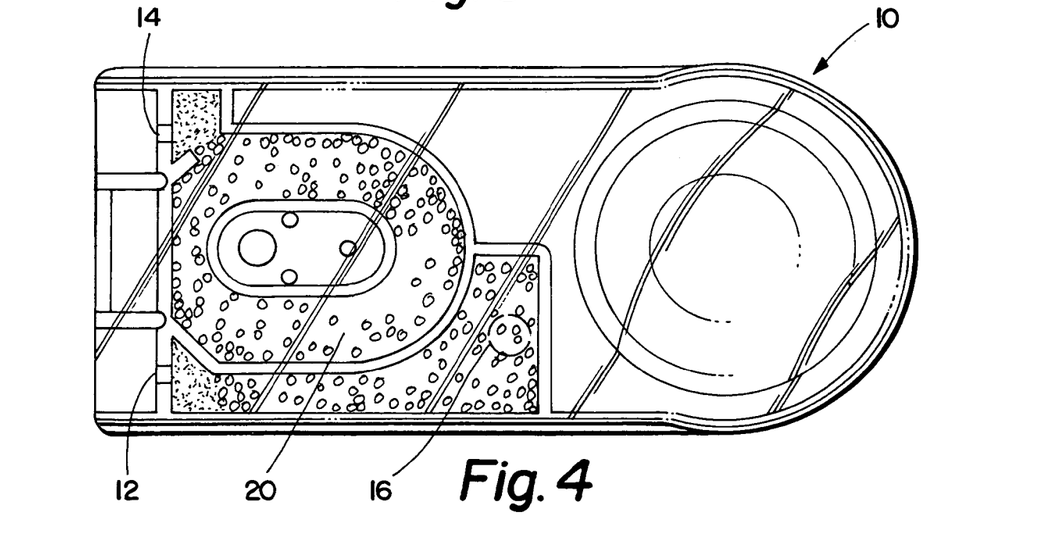
FIG. 4 is a bottom view of a sensor according to an embodiment of the present invention.
Figure 5:
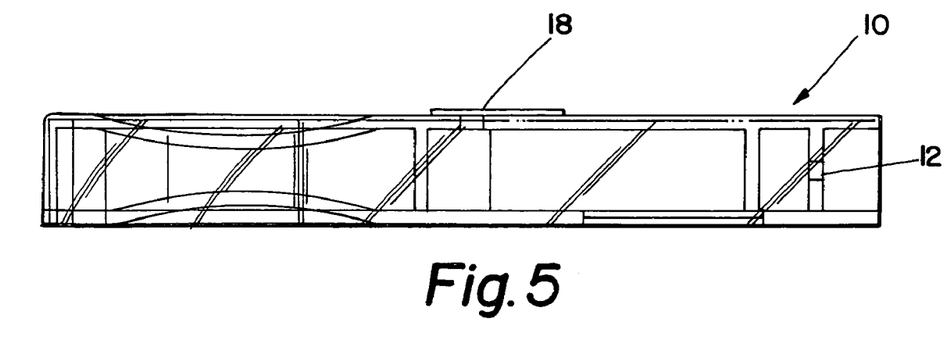
FIG. 5 is a side view of a sensor according to an embodiment of the present invention, taken from the opposite side as FIG. 3.
Figure 6:
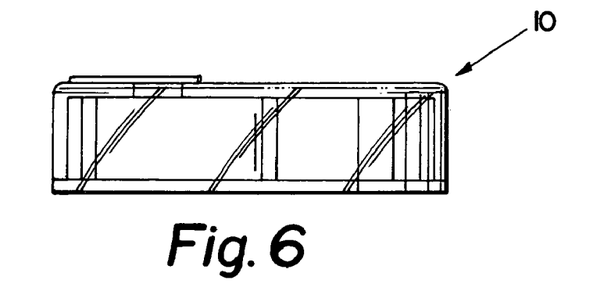
FIG. 6 is a front view of a sensor according to an embodiment of the present invention.
Figure 7:
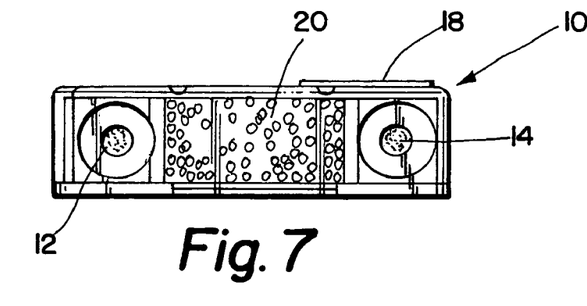
FIG. 7 is a back view of a sensor according to an embodiment of the present invention.
Figure 8:
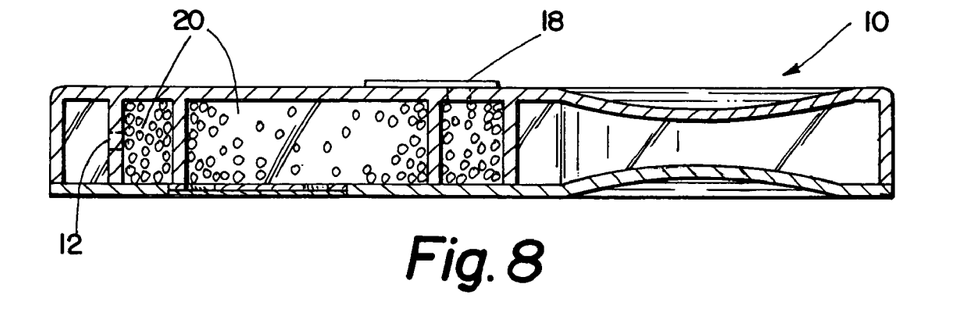
FIG. 8 is a cross section taken along line 8-8 of FIG. 2.
Figure 9:
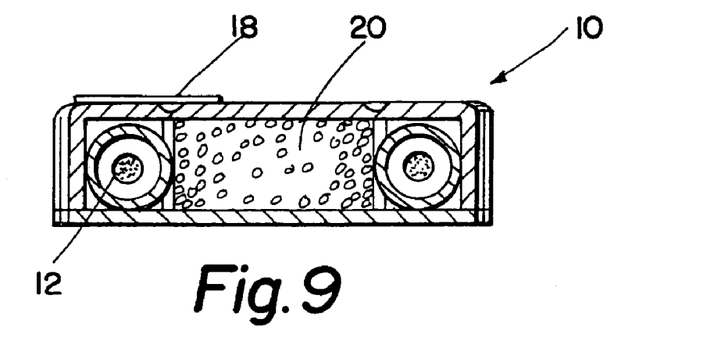
FIG. 9 is a cross section taken along line 9-9 of FIG. 2.
Figure 10:
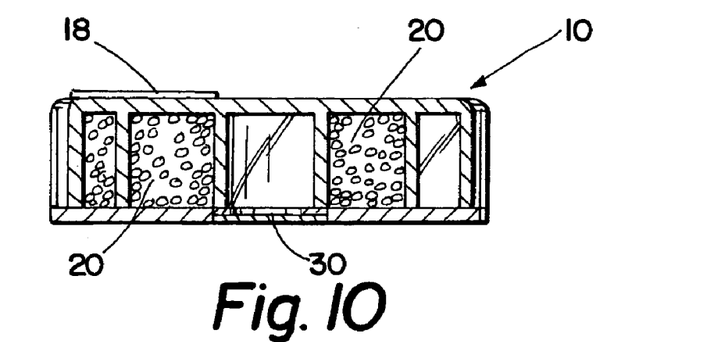
FIG. 10 is a cross section taken along line 10-10 of FIG. 2.
Figure 11:
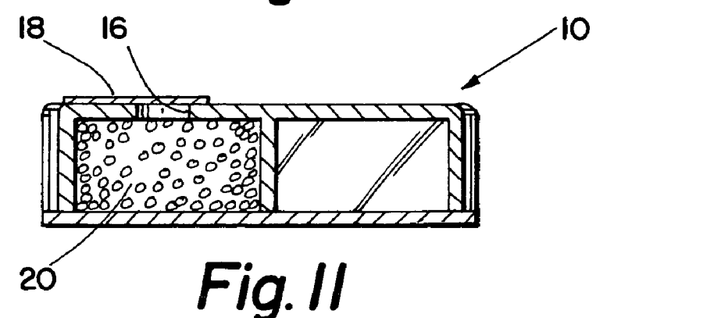
FIG. 11 is a cross section taken along 11-11 of FIG. 2.
Figure 12:
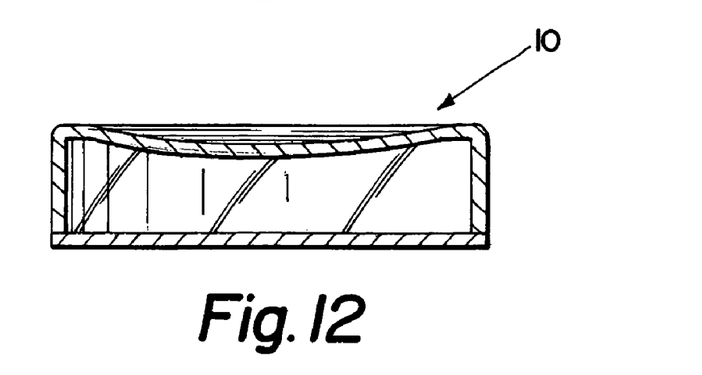
FIG. 12 is a cross section taken along line 12-12 of FIG. 2.
Figure 13:
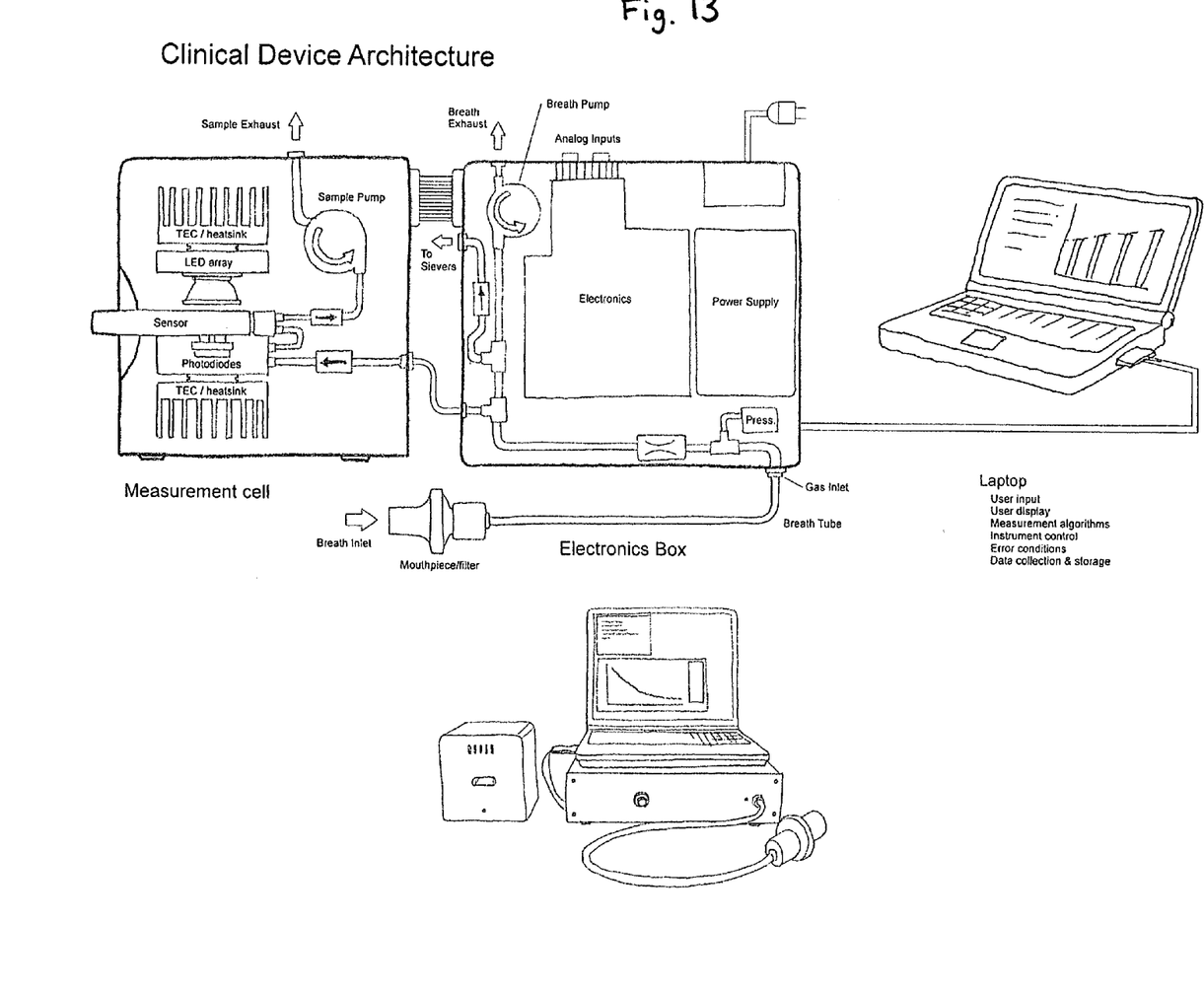
FIG. 13 is a system diagram showing a dual pump system according to an embodiment of the present invention.
Figure 14:
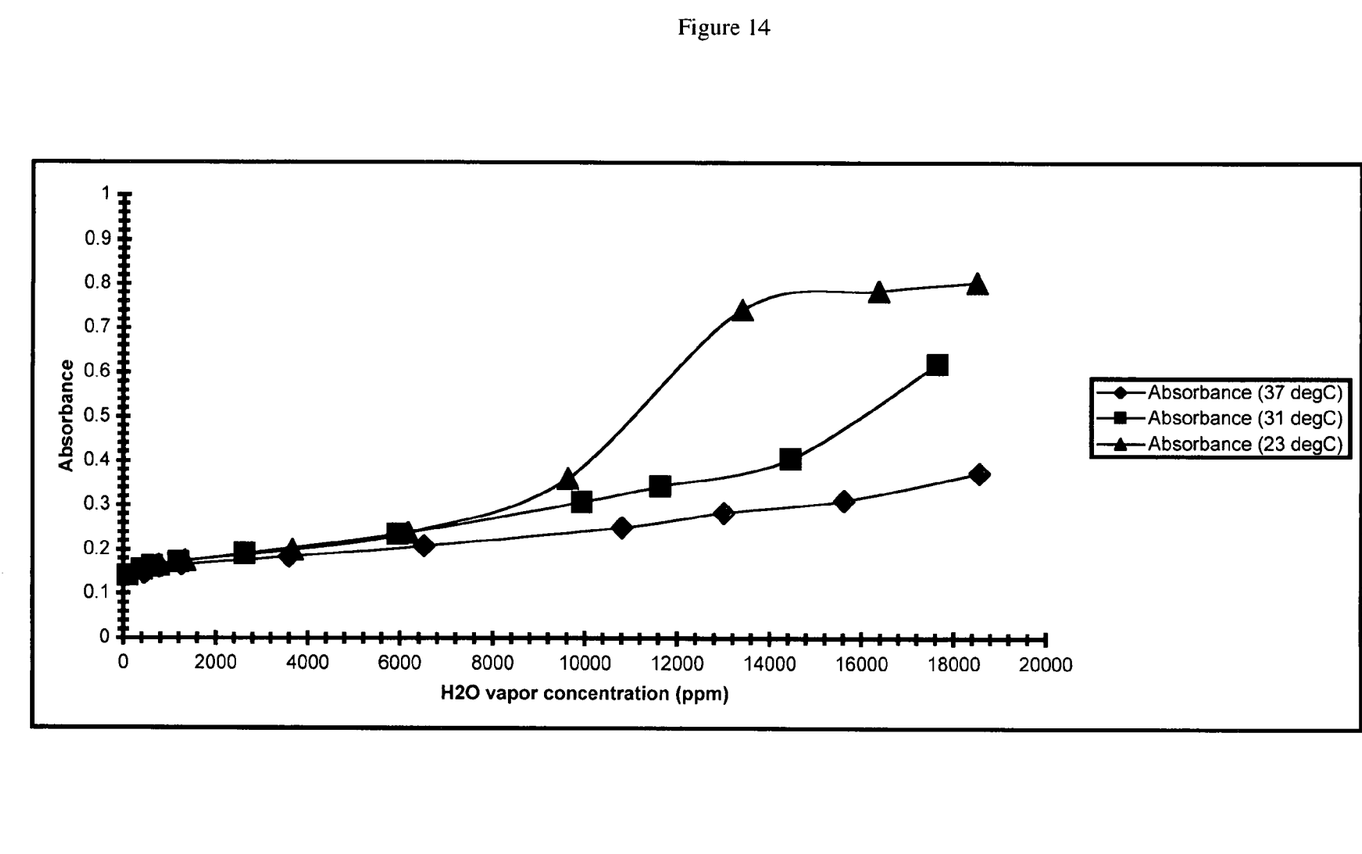
FIG. 14 is a graph of water concentration versus absorbance at various temperatures for a sensor according to an embodiment of the present invention.
Figure 15:
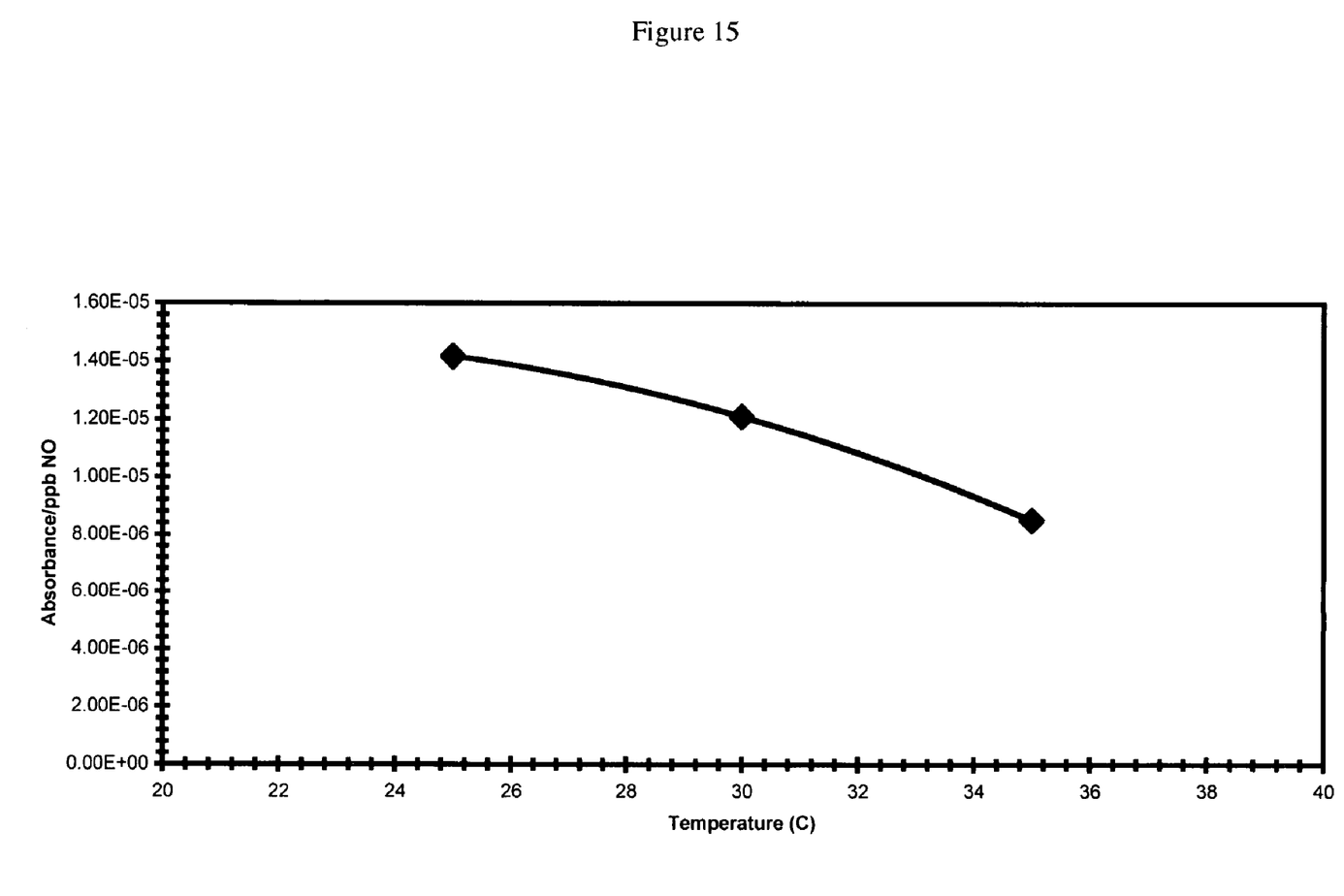
FIG. 15 is a graph of absorbance versus temperature for a sensor according to an embodiment of the present invention.

The applicants have developed a sensor for measuring nitric oxide in exhaled breath, and this sensor contains a sensing element comprised of cytochrome-c embedded in a sol-gel. See FIGS. 1-12.

As shown in the figures, the sensor has a housing 10, an entry port 12, an exit port 14, a desiccant fill hole 16, a desiccant fill hole cover 18, a desiccant 20, and a sensing element 30.

The applicants have discovered that this sensor is susceptible to humidity. In particular, the applicants discovered that a 14 ppm change in humidity causes the equivalent of a 10 ppb change in NO levels.

In addition, the applicants have discovered that with their device, nitric oxide sensitivity falls off rapidly above 1200 ppm ambient water concentration. One explanation for this is based on the Kelvin-Laplace equation. Under this explanation, the pores of the sol-gel fill with liquid water, which reduces protein accessibility to the gaseous analyte due to the poor solubility of nitric oxide in water.

It is also possible that competitive binding between nitric oxide and water causes the susceptibility of the sensor to humidity. Another potential explanation posits that nonspecific binding of water to the protein limits the attainable spectral shift of an NO binding event.

Regardless of the cause, the sensitivity of the applicant's sensor to humidity necessitates that (i) the sensor must be dried to below 1000 ppm water and (ii) the exhaled breath stream must be brought to within a few ppms of the humidity of the conditioned sensor to avoid a significant response to the water in the breath.

The applicants have also learned that it is necessary to eliminate the analyte from the air surrounding the sensor before use. Thus, for a nitric oxide sensor, it is necessary to eliminate nitric oxide from the storage environment.

Through much experimentation, the applicants have discovered that a single molecular sieve can accomplish all three goals: (i) removal of excess humidity from the storage environment, (ii) removal of nitric oxide from the storage environment, and (iii) equilibration of the incoming gas stream to the approximate humidity of the sensor. In particular the applicants have found that a 3A molecular sieve, such as one manufactured by Zeochem of Louisville, Ky., can accomplish all of these goals by itself. The molecular sieves thus serves as a desiccant and a gas stream buffer.

The molecular sieve controls the storage humidity in the sensor. In particular, it has been found that a 3A molecular sieve creates a desirable storage environment when it contains 16% water by weight. This yields the following dew points and parts per million of water at various temperatures: 35° C.: dew point: −23° C., 760 ppm; 30° C.: dew point: −29° C., 415 ppm; 15° C.: dew point: −43° C., 90 ppm. The 3A molecular sieve was chosen in part because it helps ensure that the fraction of water that the sensing element is exposed to never exceeds 1000 ppm in normal operating temperatures.

The molecular sieve also acts as scrubber, removing water from the incoming stream of exhaled breath as it enters the sensor housing. The breath sample will enter with a relative humidity equivalent to 100% of the relative humidity at the lowest temperature portion of the blow tube. The molecular sieve must scrub this stream to within a few a ppm of the water level to which the sensing element has been conditioned. In other words, the molecular sieve must equilibrate the incoming breath stream to the relatively humidity of the sensor. The 3A molecular sieve is able to serve this function as well as establishing the sensor storage humidity level.

From their experimentation, the applicants have found that a housing filled with 2.5 to 3.5 grams of 8-12 mesh 3A molecular sieve could provide sufficient scrubbing for an exhaled breath stream with a flow rate of 400 ml/min. The amount of molecular sieve required to equilibrate the incoming breath stream depends on the flow rate, time, incoming RH, size of desiccant beads, geometry of bed, and number of tests.

The molecular sieve may also serve to eliminate or reduce ambient concentrations of the analyte. For instance, if the analyte is nitric oxide, it has been found that the 3A molecular sieve can effectively reduce or eliminate concentrations of ambient nitric oxide. It is typically necessary to remove ambient concentrations of the analyte in order to ensure accurate measurement, especially if the analyte is only present in exhaled breath in trace amounts. With the 3A molecular sieve conditioned at 16% water, the decay of the response is 2E-6 AU/sec. With a sensor sensitivity of 1.85E-5 AU/ppb, this means that the sieve is catalyzing at least 0.11 ppb/sec or 6.6 ppb/min. This reaction rate allows sufficient NO to produce a sizeable signal from the measurement, but allows for the removal of NO in a reasonable time so that any subsequent tests start with essentially 0 ppb NO. Higher relative humidity will result in a slower reaction rate. Over a typical storage/delivery period of a week or more, the molecular sieves should remove substantially all of the analyte from the sensor's environment.

It is important that the analyte-removing agent (be it a molecular sieve or other means) have a reaction rate that is fast enough to effectively remove ambient concentrations of the analyte during storage, but not so fast that it removes appreciable amounts of the analyte that are exhaled by the breath.

In the embodiment emphasized in this patent the analyte-removing agent is the same as the desiccant, i.e. a molecular sieve. However, except where the claims of this patent expressly indicate otherwise, one means may be used as the desiccant, another means may be used to maintain proper humidity within the sensor, and a third may remove ambient concentrations of the analyte.

The molecular sieve should be placed upstream from the sensing element. The molecular sieve can also surround the sensor to prevent changes in water concentration.

The sensing element may also be susceptible to interference from other breath constituents besides the analyte of interest. For instance, the applicants' sensing element or monolith, comprised of cytochrome-c in a sol gel matrix, displays a significant response to carbon dioxide, which is typically present in exhaled breath in a concentration of 5%, although it can be higher. The applicants have measured this sensitivity at 70E-5 AU for 5% $CO_2$. This is equivalent to 45 ppb NO.

To remove ambient concentrations of interfering substances like carbon dioxide, a scrubber can be used, such as an 8 cm long cylinder (with a diameter of 1 cm) of activated alumina loaded to 15% water by weight can be used. This cylinder of activated alumina has a surface area of 200 m2/g. It has been found that the activated alumina at the appropriate water content can selectively remove $CO_2$, while not appreciably affecting NO concentrations.

To maintain the sensor and monolith at a predetermined temperature level ("set point"), the applicants have an installed a biphasic inline gas heater ("heater/cooler"), enabled with a Thermo-Electric Cooler controller. The heater should be in good thermal contact with the monolith or other sensing element.

The above-mentioned heater can heat the incoming gas stream at a flow rate of 400 ml/min from 24° C. to 30° C. within 0.001° C. It can also cool the sensor, if needed. Thermal management is important, since the sensor loses 4% sensitivity per degree Celsius above 30° C. The applicants have found that the average slope of a temperature dependance graph for their sensor is 4.37E-04 AU/Deg C., with a standard deviation of 2.50E-04 AU/Deg C. The temperature should be held to within 0.1° C. of the set point during testing.

In particular, the sensor is subject to thermochromic shift, and also is subject to variations in sensitivity in response to temperature changes.

The set point should be above the dew point, to prevent condensation on the optical components of the device. However, the set point should also be as low as possible to maximize the sensitivity of the sensor. As noted above, in one embodiment the set point would be 30° C.

One skilled in the art will appreciate that the present invention can be practiced by other than the preferred embodiments, which are presented for purposes of illustration and not of limitation.

We claim:

1. A system for detecting trace amounts of nitric oxide in exhaled breath, comprising:
   a. a sensing element that is responsive to a trace amount of nitric oxide in exhaled breath; and
   b. a desiccant surrounding said sensing element.

2. The system according to claim 1, wherein said desiccant is a molecular sieve.

3. The system according to claim 2, wherein said molecular sieve comprises particles having an approximate pore size of 3 Angstroms.

4. The system according to claim 1, wherein said sensing element comprises cytocbrome-c in a sol-gel.

5. The system according to claim 1, additionally comprising a scrubber for removing an interfering substance.

6. The system according to claim 5, wherein said interfering substance is carbon dioxide.

7. The system according to claim 5, wherein said scrubber comprises activated alumina.

8. The system according to claim 1, additionally comprising a heater or cooler for controlling the temperature of said sensing element.

9. A method for detecting trace amounts of nitric oxide in exhaled breath, comprising:
   a. providing a sensor, said sensor comprising a sensing element that is responsive to a trace amount of nitric oxide in exhaled breath;
   b. surrounding said sensing element with a desiccant to maintain a predetermined sensor humidity level in said sensor during storage;
   c. capturing an exhaled breath stream from a subject into said sensor; and
   d. conditioning said breath stream to a humidity level that is substantially equivalent to said predetermined sensor humidity level.

10. The method according to claim 9, wherein said desiccant is a molecular sieve.

11. The method according to claim 9, additionally comprising removing said analyte from said sensor during storage.

12. The method according to claim 11, wherein a molecular sieve is used for removing said analyte from said sensor during storage.

13. The method according to claim 9, wherein said predetermined sensor humidity level is between 10 to 1000 ppm.

14. The method according to claim 9, additionally comprising removing an interfering substance from said breath stream with a scrubber.

15. The method according to claim 14, wherein said interfering substance is carbon dioxide.

16. The method according to claim 15, wherein said scrubber comprises activated alumina.

17. A system for detecting trace amounts of nitric oxide in exhaled breath, comprising:
   a. a sensing element that is responsive to a trace amount of nitric oxide in exhaled breath;
   b. a temperature control device within sufficient proximity to said sensing element to control the temperature of said sensing element, and
   c. a molecular sieve surrounding said sensing element.

18. The system according to claim 17, wherein said temperature control device is a heater or cooler.

19. The system according to claim 18, wherein said heater or cooler maintains said exhaled breath and said sensing element at a predetermined temperature within 1.0° C.

20. The system according to claim 19, wherein said predetermined temperature is approximately 20-40 C.

21. The system according to claim 17, additionally comprising a scrubber.

* * * * *